(12) United States Patent
Angi et al.

(10) Patent No.: US 10,688,110 B2
(45) Date of Patent: *Jun. 23, 2020

(54) COMPLEXES OF CELECOXIB AND ITS SALTS AND DERIVATIVES, PROCESS FOR THE PREPARATION THEREOF AND PHARMACEUTICAL COMPOSITIONS CONTAINING THEM

(71) Applicant: NanGenex Nanotechnology Incorporated, Budapest (HU)

(72) Inventors: Erzsébet Réka Angi, Nagykovácsi (HU); Tamás Jordán, Öcsöd (HU); Richárd Balázs Kárpáti, Tatabánya (HU); Gergo Patyi, Vecsés (HU); Orsolya Basa-Dénes, Eger (HU); Tamás Solymosi, Békéscsaba (HU); Zsolt Ötvös, Csongrád (HU); László Molnár, Biatorbágy (HU); Hristos Glavinas, Szeged (HU); Genovéva Filipcsei, Budapest (HU)

(73) Assignee: NanGenex Nanotechnology Incorporated, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 16/391,764

(22) Filed: Apr. 23, 2019

(65) Prior Publication Data

US 2019/0307777 A1 Oct. 10, 2019

Related U.S. Application Data

(63) Continuation of application No. 15/380,219, filed on Dec. 15, 2016, now Pat. No. 10,307,429.

(60) Provisional application No. 62/421,723, filed on Nov. 14, 2016.

(30) Foreign Application Priority Data

Dec. 16, 2015 (HU) .................................... 1500618

(51) Int. Cl.
| | |
|---|---|
| A61K 31/415 | (2006.01) |
| C07D 231/12 | (2006.01) |
| A61K 31/635 | (2006.01) |
| A61K 45/06 | (2006.01) |
| A61K 9/14 | (2006.01) |
| A61K 9/16 | (2006.01) |
| A61K 9/00 | (2006.01) |
| A61K 9/10 | (2006.01) |
| A61K 47/20 | (2006.01) |
| B01F 3/00 | (2006.01) |
| C07D 231/10 | (2006.01) |
| A61K 9/51 | (2006.01) |

(52) U.S. Cl.
CPC ............ *A61K 31/635* (2013.01); *A61K 9/006* (2013.01); *A61K 9/0095* (2013.01); *A61K 9/10* (2013.01); *A61K 9/146* (2013.01); *A61K 9/1635* (2013.01); *A61K 9/1641* (2013.01); *A61K 31/415* (2013.01); *A61K 45/06* (2013.01); *A61K 47/20* (2013.01); *B01F 3/00* (2013.01); *C07D 231/10* (2013.01); *A61K 9/0056* (2013.01); *A61K 9/5138* (2013.01); *A61K 9/5146* (2013.01); *A61K 2300/00* (2013.01); *C07B 2200/13* (2013.01)

(58) Field of Classification Search
CPC .......................... A61K 31/415; C07D 231/12
See application file for complete search history.

(56) References Cited

U.S. PATENT DOCUMENTS

| | | | |
|---|---|---|---|
| 6,579,895 | B2 | 6/2003 | Karim |
| 8,362,062 | B2 | 1/2013 | Tawa |
| 10,307,429 | B2 | 6/2019 | Angi |
| 2002/0019431 | A1 | 2/2002 | Straub |
| 2011/0021592 | A1 | 1/2011 | Magdassi |
| 2012/0171284 | A1 | 7/2012 | Gao |

FOREIGN PATENT DOCUMENTS

| | | |
|---|---|---|
| CN | 103610649 | 3/2014 |
| CN | 103655478 | 3/2014 |
| KR | 20120053401 | 5/2012 |
| KR | 20120089817 | 8/2012 |

(Continued)

OTHER PUBLICATIONS

Abu-Diak, O. et al., "An Investigation into the Dissolution Properties of Celecoxib Melt Extrudates: Understanding the Role of Polymer Type and Concentration in Stabilizing Supersaturated Drug Concentrations", Mol Pharm., 8 (4):1362-71, (2011).

(Continued)

*Primary Examiner* — Brenda L Coleman

(74) *Attorney, Agent, or Firm* — Dennis A. Bennett; Brock D. Levin; Lauren L. Stevens

(57) ABSTRACT

Disclosed herein are stable complexes with controlled particle size, increased apparent solubility and increased dissolution rate comprising as active compound Celecoxib, its salts, or derivatives thereof, which is useful in the treatment of osteoarthritis, rheumatoid arthritis, juvenile rheumatoid arthritis, ankylosing spondylitis, acute pain especially in cancer related acute pain, primary dysmenorrhea. More specifically, the complexes possess instantaneous redispersibility, increased apparent solubility and permeability that provide faster onset of action for acute pain relief and lower GI related side effects. Further disclosed are methods of formulating and manufacturing the complexes described herein, pharmaceutical compositions, and uses and methods of treatment.

9 Claims, 22 Drawing Sheets

(56) References Cited

FOREIGN PATENT DOCUMENTS

| KR | 1237646 | | 3/2013 |
|---|---|---|---|
| WO | 2000032189 | A1 | 6/2000 |
| WO | 2001041760 | | 6/2001 |
| WO | 2001042221 | | 6/2001 |
| WO | 2001091750 | A1 | 12/2001 |
| WO | 2001095877 | A2 | 12/2001 |
| WO | 2003080027 | A1 | 10/2003 |
| WO | 2004047752 | A2 | 6/2004 |
| WO | 2004078163 | A2 | 9/2004 |
| WO | 2006003504 | | 1/2006 |
| WO | 2007010559 | A2 | 1/2007 |
| WO | 2009114695 | A1 | 9/2009 |
| WO | 2013132457 | A2 | 9/2013 |
| WO | 2014018932 | A2 | 1/2014 |
| WO | 2017103677 | A1 | 6/2017 |

OTHER PUBLICATIONS

Chowdary, K. et al., "Effect of Polyvinylpyrrolidone on Complexation and Dissolution Rate of β-Cyclodextrin and Hydroxypropyl-β-cyclodextrin Complexes of Celecoxib," Indian J Pharma Sci., 68(5):631-4, (2006).

Devi, V. et al., "Preformulation Studies on Celecoxib with a View to Improve Bioavailability", Indian Journal of Pharmaceutical Sciences, 65(5):542-5, (2003).

Dhumal, R. et al., "Development of Spray-Dried Co-Precipitate of Amorphous Celecoxib Containing Storage and Compression Stabilizers", Acta Pharm., 57(3):287-300, (2007).

Dolenc, A. et al., "Advantages of Celecoxib Nanosuspension Formulation and Transformation Into Tablets", Int J Pharmaceut., 376(1):204-12, (2009).

Gupta, P. et al., "Molecular Interactions in Celecoxib—PVP-Meglumine Amorphous System", J Pharm and Pharmacol., 57(3):303-10, (2005).

Gupta, P. et al., "Role of Molecular Interaction in Stability of Celecoxib-PVP Amorphous Systems", Mol Pharm., 2 (5):384-91, (2005).

Ha, H. et al., "Fabrication and Evaluation of Celecoxib Microparticle Surface Modified by Hydrophilic Cellulose and SM-Factant", Int J Biol Macromolecules, 72:1473-8, (2015).

International Application No. PCT/IB2016/001893; International Search Report and Written Opinion of the International Searching Authority, dated Apr. 13, 2017; 18 pages.

Knopp, M. et al., "Comparative Study of Different Methods for the Prediction of Drug-Polymer Solubility", Mol Pharm., 12(9):3408-19, (2015).

Lee, J. et al., "Enhanced Dissolution Rate of Celecoxib Using PVP and/or HPMC-Based Solid Dispersions Prepared by Spray Drying Method", J Pharm Invest., 43:205-13, (2013).

Mosquera-Giraldo, L. et al., "Impact of Surfactants on the Crystal Growth of Amorphous Celecoxib", Int J Pharm., 461(1):251-7, (2014).

Nkansah, P. et al., "Development and Evaluation of Novel Solid Nanodispersion System for Oral Delivery of Poorly Water-Soluble Drugs", J Control Release, 169(1):150-61, (2013).

Pawar, V. et al., "Engineered Nanocrystal Technology: In-Vivo Fate, Targeting and Applications in Drug Delivery", J Control Release, 183:51-66, (2014).

Shakeel, F. et al., "Nanoemulsion: A Promising Tool for Solubility and Dissolution Enhancement of Celecoxib", Pharma Develop Tech., 15(1):53-6, (2010).

U.S. Appl. No. 15/380,219; Non-Final Office Action, dated Dec. 12, 2017; 8 pages.

U.S. Appl. No. 15/380,219; Non-Final Office Action, dated May 11, 2018; 7 pages.

U.S. Appl. No. 15/380,219; Notice of Allowance, dated Jan. 24, 2019; 14 pages.

FIG. 1

| | | Pharmaceutically acceptable excipient | | | | | | | | | | | | | | |
|---|---|---|---|---|---|---|---|---|---|---|---|---|---|---|---|---|
| | | Citric Acid | CPC | D-Mannitol | DSS | Kollicoat-IR | Lutrol F127 | Luviquat MS370 | Luviquat PQ11PN | Meglumine | NaOAc | NONE | Pluronic PE10500 | SDC | SDS | Solutol HS15 | Lactose |
| Complexation agent | Gelucire 44/14 | + | + | - | + | - | - | - | - | - | - | - | + | - | - | + | - |
| | Gelucire 50/13 | - | + | - | + | - | - | - | - | - | - | - | + | - | - | - | - |
| | Klucell EF | + | + | - | + | - | - | - | - | - | - | - | + | - | + | - | - |
| | Poloxamer 407 | + | + | + | + | + | + | + | + | + | + | + | + | + | + | - | + |
| | Kollidon VA64 | + | + | - | + | - | + | - | - | - | - | - | + | + | - | - |
| | PEOX50 | - | + | - | - | - | - | - | - | - | - | - | - | - | - | - | - |
| | PEOX500 | + | - | - | - | - | + | - | - | - | - | - | - | - | + | - | - |
| | Plasdone K-12 | + | + | - | + | - | + | - | - | + | - | - | + | + | - | - | - |
| | Poloxamer 335 | + | + | - | + | - | + | - | - | - | - | + | + | + | + | + | + |
| | Poloxamer 188 | + | + | - | + | + | - | - | - | + | + | - | - | + | + | - | - |
| | Poloxamer 338 | + | + | + | + | - | + | - | - | - | + | - | - | + | + | - | - |
| | PMAMVE | - | - | - | - | - | + | - | - | - | - | - | - | - | - | - | - |
| | PVP 40 | - | - | - | + | - | - | - | - | - | - | - | - | - | + | - | - |
| | PVP K90 | + | + | - | + | - | - | - | - | - | - | - | - | - | + | - | - |
| | PVP 10 | + | - | - | + | - | - | - | + | - | - | - | - | + | + | - | - |
| | Soluplus | + | - | - | - | - | - | - | - | - | - | - | - | - | + | - | - |
| | Tetronic 1107 | + | + | + | + | + | + | + | + | + | + | + | + | - | + | - | + |
| | TPGS | + | + | + | + | + | + | + | + | - | + | + | + | + | + | + | + |
| | + redispersable solid Celecoxib complex in ultrapurified water<br>- non-redispersable solid Celecoxib complex in ultrapurified water | | | | | | | | | | | | | | | | |

FIG. 2

| | | Pharmaceutically acceptable excipient | | | | | | | | | | | | | | |
|---|---|---|---|---|---|---|---|---|---|---|---|---|---|---|---|---|
| | | Citric Acid | CPC | D-Mannitol | DSS | Kollicoat-IR | Lactose | Lutrol F127 | Luviquat MS370 | Luviquat PQ11PN | Meglumine | NaOAc | NONE | Pluronic PE10500 | SDC | SDS | Solutol HS15 |
| Complexation agent | Gelucire 44/14 | - | - | - | - | - | - | - | - | - | - | - | - | + | - | - | - |
| | Gelucire 50/13 | - | - | - | - | - | - | + | + | + | - | - | - | + | - | + | - |
| | Klucell EF | - | - | - | - | - | - | - | - | - | - | - | - | - | - | + | - |
| | Klucell LF | - | - | - | + | - | - | - | - | - | - | - | - | - | - | + | - |
| | Poloxamer 407 | + | + | + | + | + | + | + | + | + | + | + | + | + | + | + | + |
| | Kollidon VA64 | - | + | - | + | - | + | + | - | - | - | - | - | - | - | + | - |
| | NONE | - | - | - | - | - | - | - | - | - | - | - | - | - | - | - | - |
| | PEG2000 | - | - | - | - | - | - | - | - | - | - | - | - | - | - | - | - |
| | PEOX200 | - | - | - | - | - | - | - | - | - | - | - | - | - | - | + | - |
| | PEOX50 | - | + | - | - | - | - | - | - | - | - | - | - | - | - | + | - |
| | PEOX500 | - | + | - | - | - | + | - | - | - | - | - | - | - | - | + | - |
| | Plasdone K-12 | - | + | - | - | - | - | - | - | - | - | - | - | - | + | + | - |
| | Poloxamer 335 | - | + | - | + | - | - | - | - | - | + | - | - | - | + | + | - |
| | Poloxamer 188 | - | - | - | + | - | + | + | - | - | - | - | - | - | + | + | - |
| | Poloxamer 338 | + | + | + | + | - | - | + | - | - | + | + | + | - | + | + | + |
| | PMAMVE | - | - | - | - | - | - | - | - | - | - | - | - | - | - | - | - |
| | PVP 40 | - | - | - | - | - | - | - | - | - | - | - | - | - | - | + | - |
| | PVP K90 | - | + | - | - | - | - | - | - | - | - | - | - | - | - | + | - |
| | PVP 10 | - | + | - | + | - | - | - | - | - | - | - | - | - | - | + | - |
| | Soluplus | - | - | - | - | - | - | - | + | - | - | - | - | + | - | - | - |
| | Tetronic 1107 | + | + | + | - | - | + | + | + | + | + | + | + | + | + | + | + |
| | TPGS | + | - | + | - | + | + | + | + | + | + | - | + | + | + | + | + |

+ redispersable solid Celecoxib complex in simulated saliva (pH=6.8)
- non-redispersable solid Celecoxib complex in simulated saliva (pH=6.8

FIG. 3

| Solvent | Complexation agent | Pharmaceutically acceptable excipient | Redispersibility | PAMPA permability in water (x10-6 cm/s) |
|---|---|---|---|---|
| Methanol | PVP K90 | DSS | + | 1.81 |
| Methanol | PVP 40 | SDS | + | 1.98 |
| Methanol | Luviskol VA64 | SDS | + | 1.68 |
| Methanol | Luviskol VA64 | Lutrol F127 | + | 0.98 |
| Methanol | Tetronic | None | + | 1.38 |
| EtOH | Luviskol VA64 | SDS | + | 2.06 |
| EtOH | Tetronic | None | + | 1.44 |
| EtOH | Tetronic | D-mannitol | + | 1.42 |
| NPA | Pluronic PE10500 | SDS | + | 1.30 |
| NPA | Lutrol F127 | Lactose | + | 1.09 |
| IpOH | Luviskol VA64 | SDS | + | 1.83 |
| ACN | Tetronic | None | + | 1.37 |
| ACN | Tetronic | D-mannitol | + | 1.38 |

FIG. 4

| Composition optimization | | | | | | |
|---|---|---|---|---|---|---|
| Celecoxib concentration (mg/mL) | PVP concentration (mg/mL) | SDS concentration (mg/mL) | Flow rate ratio of solutions | Flow rate of solution 2 (ml/min) | Appearance of produced solution mixture | Stability of redispersed complex |
| 2 | 4 | 0.3 | 1:4 | 10 | | 4 h |
| 2 | 4 | 0.3 | 1:4 | 5 | | 5 min |
| 2 | 4 | 0.3 | 1:4 | 5 | Visible crystals | > 4 h |
| 2 | 4 | 0.35 | 1:4 | 5 | Visible crystals | > 4 h |
| 2 | 4 | 0.4 | 1:4 | 5 | Visible crystals | Opalescent after 30 min |
| 2* | 4 | 0.45 | 1:4 | 5 | Opalescent solution | > 4 h |
| 2 | 4 | 0.5 | 1:4 | 5 | Opalescent solution | > 4 h |

*Selected composition*

FIG. 5

| Celecoxib concentration (mg/mL) | PVP concentration (mg/mL) | SDS concentration (mg/mL) | Ratio of solutions (MeOH:Water) | Stability of produced solution mixture |
|---|---|---|---|---|
| 10 | 20 | 2.25 | 1:4 | 10 min |
| 5 | 10 | 1.125 | 1:4 | 10 min |
| 2.5 | 5 | 0.5625 | 1:4 | 10 min |
| 1.25 | 2.5 | 0.2812 | 1:4 | 10 min |
| 5 | 10 | 9 | 2:1 | > 2h |
| 10* | 20 | 18 | 2:1 | > 2h |

* Selected composition – optimal production parameters

FIG. 6

| Celecoxib concentration (mg/mL) | Copolymer of vinylpirrolidon and vinylacetate concentration (mg/mL) | SDS concentration (mg/mL) | Ratio of Solution 1 and Solution 2 | Stability of produced solution mixture |
|---|---|---|---|---|
| 10 | 40 | 2.5 | 1:4 | 40 min |
| 10 | 40 | 5 | 1:2 | 30 min |
| 10 | 40 | 10 | 1:1 | > 1h |
| 10 | 40 | 20 | 2:1* | > 1 day |

*Selected composition — optimal production parameters*

FIG. 7

| Celecoxib concentration (mg/mL) | Copolymer of vinylpirrolidon and vinylacetate concentration (mg/mL) | SDS concentration (mg/mL) | Flow rate ratio of solutions | Flow rate (mL/min) | Appearance of produced solution mixture |
|---|---|---|---|---|---|
| 13.33 | 53.33 | 13.33 | 1:1 | 2 | not mixed |
| 13.33 | 53.33 | 13.33 | 1:1 | 4 | not mixed |
| 13.33 | 53.33 | 13.33 | 1:1 | 10 | not mixed |
| 13.33 | 53.33 | 13.33 | 1:1 | 20 | not mixed |
| 13.33 | 53.33 | 13.33 | 1:1 | 40 | clear solution |
| 13.33 | 53.33 | 13.33 | 1:1 | 60 | clear solution |
| 13.33 | 53.33 | 13.33 | 1:1 | 80 | clear solution |
| 10 | 40 | 20 | 2:1 | 3 | not mixed |
| 10 | 40 | 20 | 2:1 | 6 | not mixed |
| 10 | 40 | 20 | 2:1 | 15 | not mixed |
| 10 | 40 | 20 | 2:1 | 30 | not mixed |
| 10 | 40 | 20 | 2:1 | 45 | not mixed |
| 10* | 40 | 20 | 2:1 | 60 | clear solution |
| 10 | 40 | 20 | 2:1 | 75 | clear solution |

*Selected production parameters*

FIG. 8

| Formulation | t (min) | Dissolution (%) | Formulation | t (min) | Dissolution (%) |
|---|---|---|---|---|---|
| Physical mixture of Celecoxib, polyvinylpyrrolidone and SDS | 1 | 1.007 | Complex Celecoxib formulation containing polyvinylpyrrolidone and SDS | 1 | 93.429 |
| | 3 | 0.854 | | 3 | 94.571 |
| | 5 | 0.614 | | 5 | 79.500 |
| | 10 | 0.875 | | 10 | 95.000 |
| | 20 | 0.861 | | 20 | 80.107 |
| | 30 | 0.871 | | 30 | 85.821 |
| Physical mixture of Celecoxib, copolymer of vinylpyrrolidone and vinylacetate and SDS | 1 | 2.296 | Complex Celecoxib formulation containing copolymer of vinylpyrrolidone and vinylacetate and SDS | 1 | 81.107 |
| | 3 | 3.471 | | 3 | 99.821 |
| | 5 | 3.929 | | 5 | 95.179 |
| | 10 | 4.161 | | 10 | 98.893 |
| | 20 | 5.493 | | 20 | 92.042 |
| | 30 | 6.068 | | 30 | 91.170 |
| Physical mixture of Celecoxib, poloxamer and lactose | 1 | 1.154 | Complex Celecoxib formulation containing poloxamer and lactose | 1 | 80.357 |
| | 3 | 2.082 | | 3 | 78.714 |
| | 5 | 2.096 | | 5 | 73.071 |
| | 10 | 2.243 | | 10 | 99.036 |
| | 20 | 2.775 | | 20 | 78.393 |
| | 30 | 3.032 | | 30 | 10.179 |
| Unformulated crystalline Celecoxib | 1 | 0.475 | Celebrex® | 1 | 1.300 |
| | 3 | 0.454 | | 3 | 0.436 |
| | 5 | 0.711 | | 5 | 0.457 |
| | 10 | 0.518 | | 10 | 0.386 |
| | 20 | 0.414 | | 20 | 0.304 |
| | 30 | 0.486 | | 30 | 0.421 |

FIG. 9

| Composition | PAMPA permeability ($\times 10^{-6}$ cm/s) |
|---|---|
| Complex Celecoxib formulation containing polyvinylpyrrolidone and SDS | 1.4467 |
| Complex Celecoxib formulation containing copolymer of vinylpyrrolidone and vinylacetate and SDS | 0.8774 |
| Complex Celecoxib formulation containing poloxamer and lactose | 0.5946 |
| Unformulated Celecoxib | 0.3218 |

FIG. 10

|  | PAMPA permeability (x10$^{-6}$ cm/s) | | |
| --- | --- | --- | --- |
|  | in water | in FaSSIF | in FeSSIF |
| Unformulated Celecoxib | 0 | 0.0539 | 0.1604 |
| Celebrex (200 mg) capsule | 0.1706 | 0.1043 | 0.1897 |
| Complex Celecoxib formulation containing polyvinylpyrrolidone and SDS | 2.3941 | 1.9843 | 1.7898 |
| Spray dried complex Celecoxib formulation containing polyvinylpyrrolidone and SDS | 2.6988 | 2.2632 | 3.0918 |
| Dry granulated complex Celecoxib formulation containing polyvinylpyrrolidone and SDS | 3.0201 | 2.5970 | 2.8108 |

FIG. 11

|  | PAMPA permeability (x10$^{-6}$ cm/s) | | |
| --- | --- | --- | --- |
|  | in water | in FaSSIF | in FeSSIF |
| Unformulated Celecoxib | 0 | 0.054 | 0.160 |
| Celebrex (200 mg) capsule | 0.171 | 0.104 | 0.190 |
| Complex Celecoxib formulation containing copolymer of vinylpyrrolidone and vinyl acetate and SDS | 2.853 | n.m. | n.m. |
| Spray dried complex Celecoxib formulation containing copolymer of vinylpyrrolidone and vinyl acetate and SDS | 2.595 | 2.295 | 2.454 |
| Dry granulated complex Celecoxib formulation containing copolymer of vinylpyrrolidone and vinyl acetate and SDS | 2.597 | 2.123 | 2.514 |

FIG. 12

|  | PAMPA permeability in water (x10⁻⁶ cm/s) Time | | | |
|---|---|---|---|---|
|  | 1 day | | 30 days | |
|  | RT | 40°C | RT | 40°C |
| Freeze dried complex Celecoxib formulation containing polyvinylpyrrolidone and SDS | 2.394 | 2.394 | 2.216 | 1.960 |
| Spray dried complex Celecoxib formulation containing polyvinylpyrrolidone and SDS | 3.158 | 3.158 | 3.164 | 3.104 |
| Dry granulated complex Celecoxib formulation containing polyvinylpyrrolidone and SDS | 2.554 | 2.554 | 3.242 | 3.315 |

FIG. 13

|  | PAMPA permeability in water (x10⁻⁶ cm/s) Time | | | | | |
|---|---|---|---|---|---|---|
|  | 1 day | | 30 days | | 6 months | |
|  | RT | 40°C | RT | 40°C | RT | 40°C |
| Freeze dried complex Celecoxib formulation containing copolymer of vinylpyrrolidone and vinyl acetate and SDS - (R&D batch) | 2.8525 | | Not measured | | | |
| Spray dried complex Celecoxib formulation containing copolymer of vinylpyrrolidone and vinyl acetate and SDS - (cGMP CMC batch) | 2.595 | n.m. | 2.965 | 2.430 | 2.092 | 1.890 |
| Dry granulated complex Celecoxib formulation containing copolymer of vinylpyrrolidone and vinyl acetate and SDS -(cGMP CMC batch) | 2.597 | n.m. | 2.496 | 2.269 | 2.351 | 2.512 |

- - - - Spray-dried Celecoxib containing copolymer of vinylpirrolidon and vinyl acetate and sodium-lauryl sulphate - 40°C 6 months
- - - Dry granuled Celecoxib containing copolymer of vinylpirrolidon and vinyl acetate and sodium-lauryl sulphate - 40°C 6 months
········ Kollidon VA 64
———— SDS
- · - Reference-API FIG. 15A 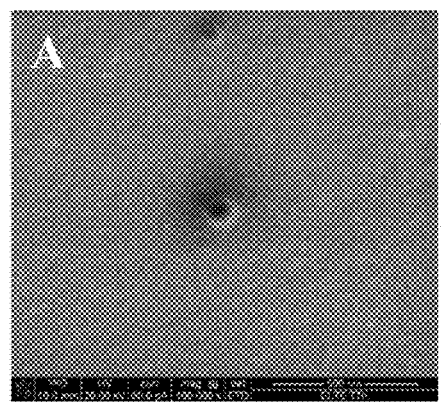 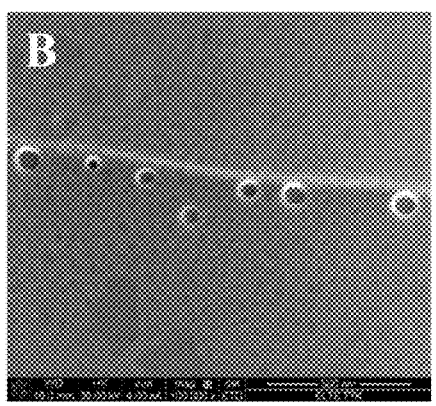 FIG. 15B
FIG. 15C

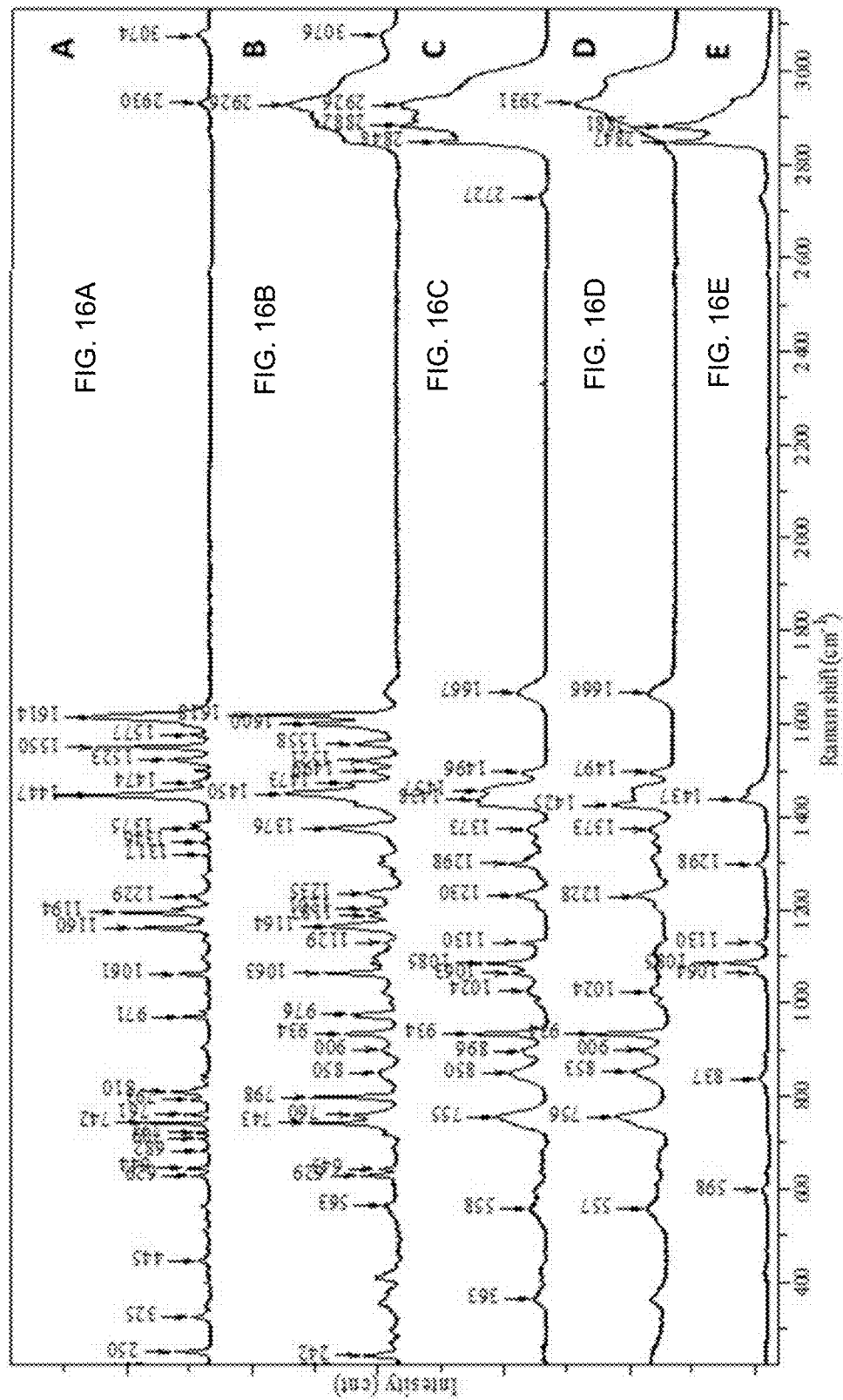

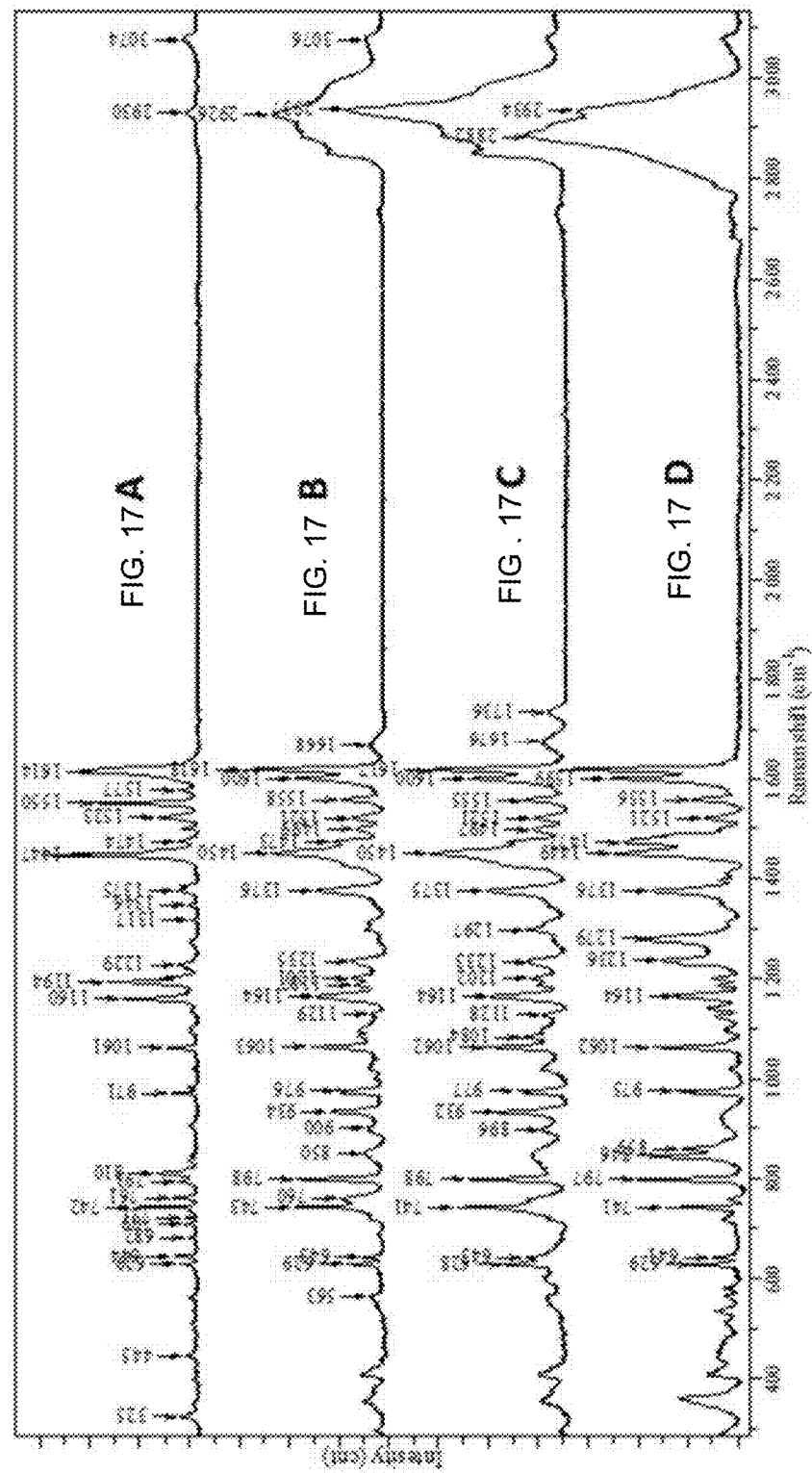

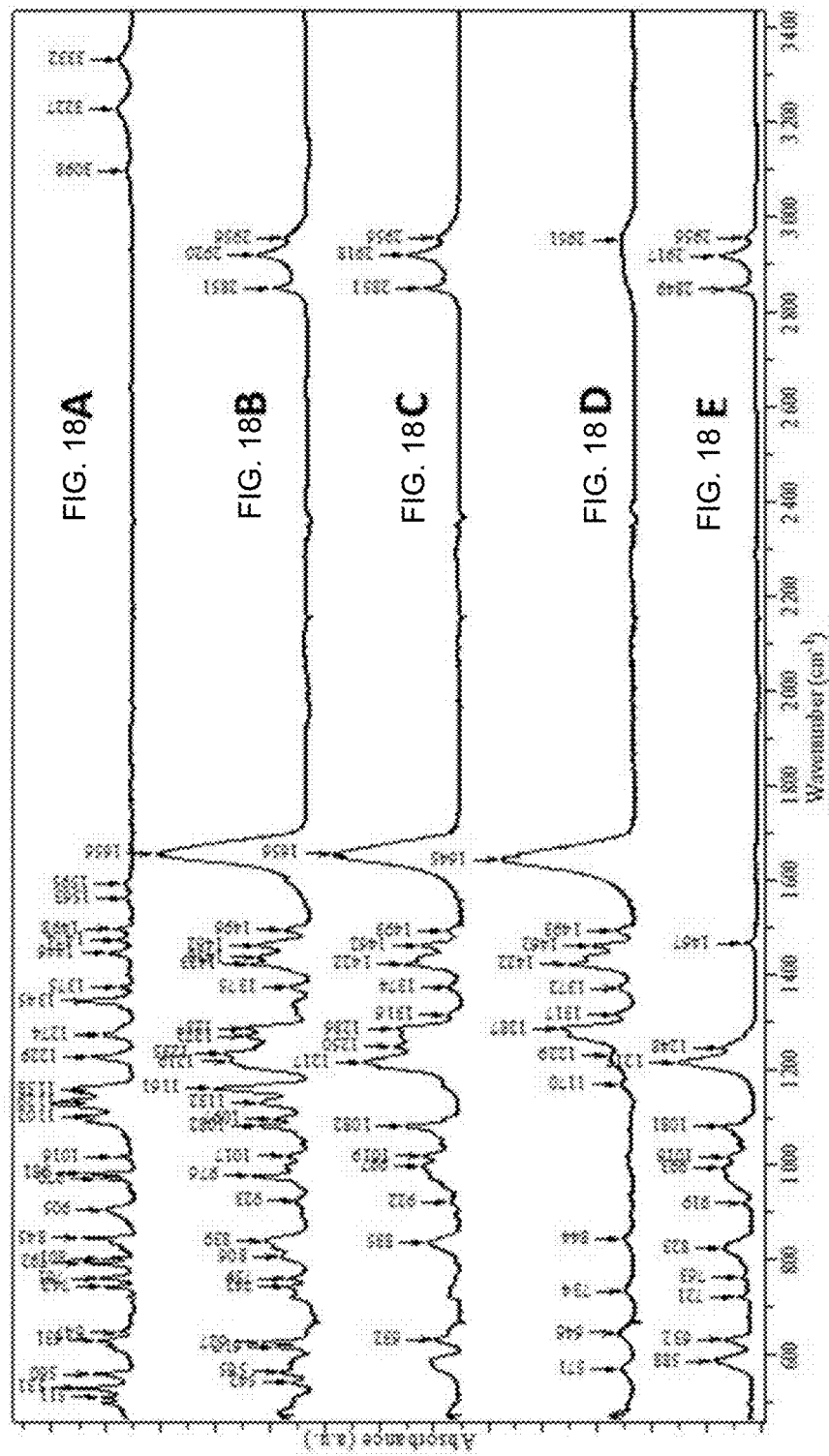

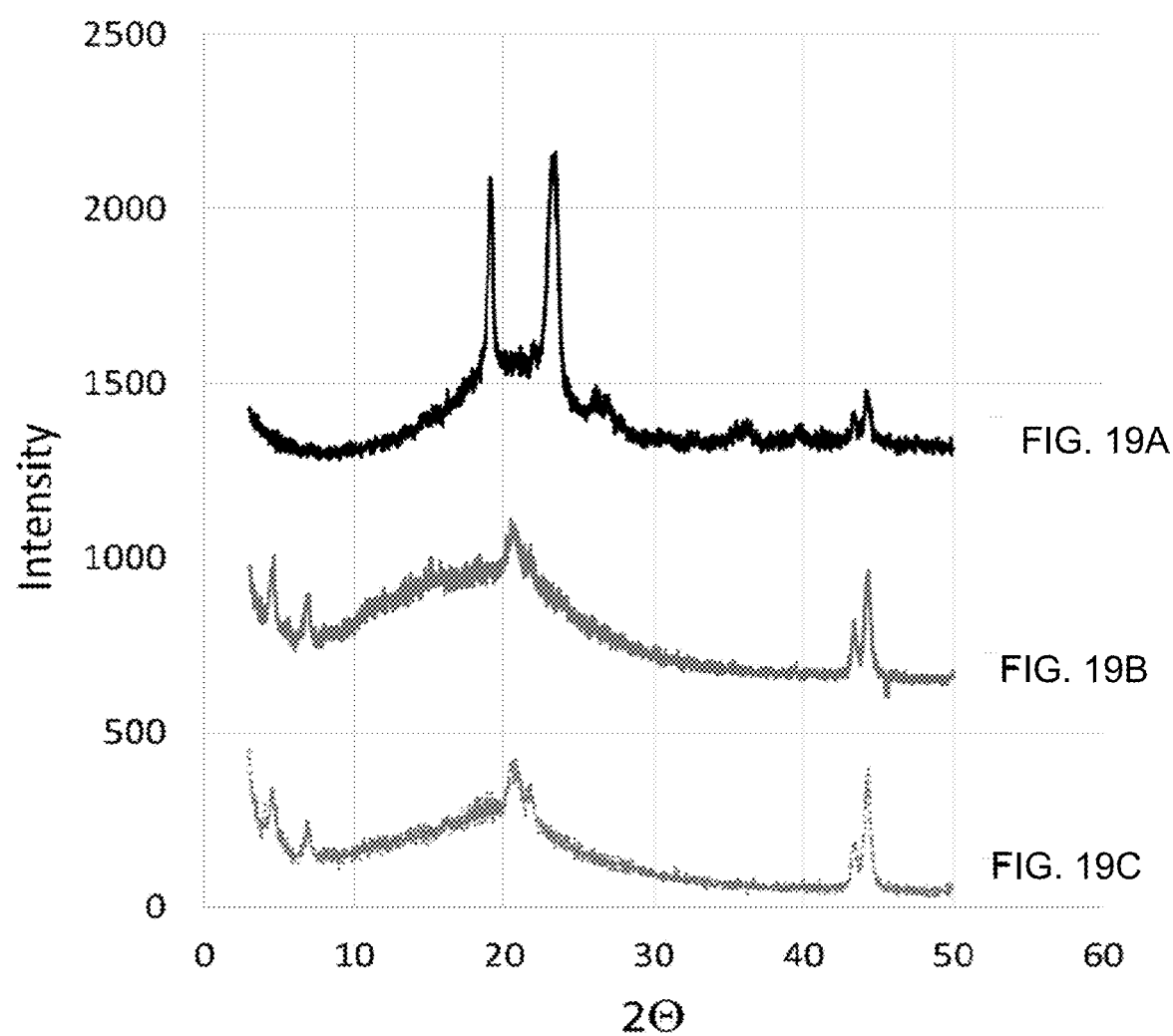

FIG. 20

| Treatment | $t_{max}$ (h) | $C_{max}$ (μg/ml) | AUC (μg/ml*h) |
|---|---|---|---|
| Complex Celecoxib formula administered under the tongue of the animals | 1-2 | 0.66 ± 0.20 | 6.1 ± 2.9 |
| Complex Celecoxib formulation administered orally | 0.5 | 1.37 ± 0.42 | 8.5 ± 3.2 |

FIG. 21

| Treatment | Feeding | $t_{max}$ (h) | $C_{max}$ (μg/ml) | AUC (μg/ml*h) |
|---|---|---|---|---|
| 5 mg/kg Complex Celecoxib formulation | Fasted | 0.75 | 1.62 ± 0.2 | 8.1 ± 2.9 |
| | High fat | 1.0 | 1.43 ± 0.3 | 7.8 ± 2.9 |

FIG. 22

| Test article | Dose (mg) | Feeding condition | $t_{max}$ (h) | $t_{250\,ng/ml}$ (h) | $C_{max}$ (ng/ml) | $AUC_{last}$ (h*ng/ml) |
|---|---|---|---|---|---|---|
| Complex Celecoxib formulation | 200 | Fasted | 0.75 ± 0.18 | 0.19 | 1586 ± 481 | 6047 ± 1648 |
| | 200 | High fat breakfast | 2.02 ± 1.36 | 0.20 | 867 ± 257 | 6197 ± 1536 |

COMPLEXES OF CELECOXIB AND ITS SALTS AND DERIVATIVES, PROCESS FOR THE PREPARATION THEREOF AND PHARMACEUTICAL COMPOSITIONS CONTAINING THEM

This application is a continuation of U.S. patent application Ser. No. 15/380,219, filed Dec. 15, 2016, which claims priority to U.S. patent application No. 62/421,723, filed Nov. 14, 2016, and application no. HU P1500618, filed Dec. 16, 2015, the disclosures of which are hereby incorporated by reference as if written herein in their entireties.

FIELD OF THE INVENTION

Disclosed herein are stable complexes with controlled particle size, increased apparent solubility and increased dissolution rate comprising as active compound Celecoxib, its salts, or derivatives thereof, which is useful in the treatment of osteoarthritis, rheumatoid arthritis, juvenile rheumatoid arthritis, ankylosing spondylitis, acute pain especially in cancer related acute pain, primary dysmenorrhea. More specifically, the complexes possess instantaneous redispersibility, increased apparent solubility and permeability that provide faster onset of action for acute pain relief and lower GI related side effects. Further disclosed are methods of formulating and manufacturing the complexes described herein, pharmaceutical compositions, and uses and methods of treatment.

BACKGROUND OF THE INVENTION

The chemical name of Celecoxib is 4-[5-(4-methylphenyl)-3-(trifluoromethyl)-1H-pyrazol-1-yl] benzenesulfonamide and is a diaryl-substituted pyrazole. The molecular formula is $C_{17}H_{14}F_3N_3O_2S$, and the molecular weight is 381.38; the chemical structure is as follows:

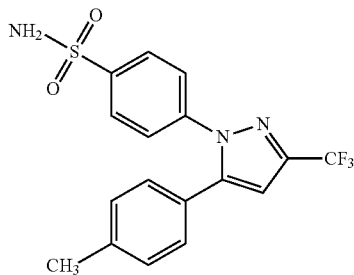 [SMILES: Cc1ccc(-c2cc(C(F)(F)F)nn2-c2ccc(S(N)(=O)=O)cc2)cc1]

Celecoxib is a white powder; insoluble in water; soluble in methanol and chloroform.

CELEBREX oral capsules contain either 50 mg, 100 mg, 200 mg or 400 mg of Celecoxib, together with inactive ingredients including: croscarmellose sodium, edible inks, gelatin, lactose monohydrate, magnesium stearate, povidone and sodium lauryl sulfate.

CELEBREX is a nonsteroidal anti-inflammatory drug that exhibits anti-inflammatory, analgesic, and antipyretic activities in animal models. The mechanism of action of CELEBREX is believed to be due to inhibition of prostaglandin synthesis, primarily via inhibition of cyclooxygenase-2 (COX-2), and at therapeutic concentrations in humans, CELEBREX does not inhibit the cyclooxygenase-1 (COX-1) isoenzyme. In animal colon tumor models, CELEBREX reduced the incidence and multiplicity of tumors.

Peak plasma levels of Celecoxib occur approximately 3 hrs after an oral dose. Under fasting conditions, both peak plasma levels ($C_{max}$) and area under the curve (AUC) are roughly dose-proportional up to 200 mg BID; at higher doses there are less than proportional increases in $C_{max}$ and AUC. Absolute bioavailability studies have not been conducted. With multiple dosing, steady-state conditions are reached on or before Day 5.

When CELEBREX capsules were taken with a high fat meal, peak plasma levels were delayed for about 1 to 2 hours with an increase in total absorption (AUC) of 10% to 20%. Under fasting conditions, at doses above 200 mg, there is less than a proportional increase in $C_{max}$ and AUC, which is thought to be due to the low solubility of the drug in aqueous media.

Coadministration of CELEBREX with an aluminum- and magnesium-containing antacids resulted in a reduction in plasma celecoxib concentrations with a decrease of 37% in $C_{max}$ and 10% in AUC. CELEBREX, at doses up to 200 mg twice daily, can be administered without regard to timing of meals. Higher doses (400 mg twice daily) should be administered with food to improve absorption.

In healthy adult volunteers, the overall systemic exposure (AUC) of Celecoxib was equivalent when Celecoxib was administered as intact capsule or capsule contents sprinkled on applesauce. There were no significant alterations in $C_{max}$, $t_{max}$ or $t_{1/2}$ after administration of capsule contents on applesauce.

In healthy subjects, Celecoxib is highly protein bound (~97%) within the clinical dose range. In-vitro studies indicate that Celecoxib binds primarily to albumin and, to a lesser extent, α1-acid glycoprotein. The apparent volume of distribution at steady state (Vss/F) is approximately 400 L, suggesting extensive distribution into the tissues. Celecoxib is not preferentially bound to red blood cells.

Celecoxib metabolism is primarily mediated via CYP2C9. Three metabolites, a primary alcohol, the corresponding carboxylic acid and its glucuronide conjugate, have been identified in human plasma. These metabolites are inactive as COX-1 or COX-2 inhibitors.

Celecoxib is eliminated predominantly by hepatic metabolism with little (<3%) unchanged drug recovered in the urine and feces. Following a single oral dose of radiolabeled drug, approximately 57% of the dose was excreted in the feces and 27% was excreted into the urine. The primary metabolite in both urine and feces was the carboxylic acid metabolite (73% of dose) with low amounts of the glucuronide also appearing in the urine. It appears that the low solubility of the drug prolongs the absorption process making terminal half-life (t½) determinations more variable. The effective half-life is approximately 11 hours under fasted conditions. The apparent plasma clearance (CL/F) is about 500 mL/min.

The main medical concerns surrounding Celecoxib are related to slow absorption and variable first-pass metabolism of Celecoxib limit its utility for treatment of acute pain. When a single dose of 200 mg of current formulation is given, peak plasma levels occur 3 hours after an oral dose, however, onset of pain relief could be as early as 1 hour. When taken with a high fat meal, peak plasma levels are delayed for about 1 to 2 hours with an increase in total absorption (AUC) of 10% to 20%. Since it is a painkiller shortening this time and the elimination of the delay of peak plasma concentrations could be advantageous.

In order to overcome the problems associated with prior conventional Celecoxib formulations and available drug delivery systems, novel complex formulations of Celecoxib or its salts or its derivatives thereof and complexation agents and pharmaceutically acceptable excipients were prepared. Said complex formulations are characterized by instantaneous redispersibility, increased apparent solubility, instantaneous dissolution, increased permeability that provide faster onset of action for acute pain relief and lower GI related side effects compared to the currently available formulations.

A variety of strategies have been used to attempt to overcome these issues, see for example US 20130338131, WO 2009114695, U.S. Pat. No. 7,879,360, US 20090098200, WO 2003080027, US 20150011514, U.S. Pat. Nos. 6,964,978, 7,220,867, WO 2001042221, WO 2001095877, WO 2001091750, WO 2014018932, WO 2004078163, WO 2004047752, WO 2007010559, WO 2013132457 and WO 2001041760.

DESCRIPTION OF THE INVENTION

Disclosed herein are stable complexes comprising an active compound chosen from Celecoxib, its salts or derivatives thereof; and at least one complexation agent chosen from polyethylene glycol glycerides composed of mono-, di- and triglycerides and mono- and diesters of polyethylene glycol (e.g.; Gelucire 44/14, Gelucire 50/13), hydroxypropylcellulose (e.g; Klucell EF, Klucell LF), poloxamers (copolymers of ethylene oxide and propylene oxide blocks) (e.g; Poloxamer 407, Poloxamer 335, Poloxamer 188, Poloxamer 338), vinylpyrrolidone/vinyl acetate copolymer (e.g.; Kollidon VA64), poly(2-ethyl-2-oxazoline) (e.g; PEOX50, PEOX500), polyvinylpyrrolidone (e.g; Plasdone K-12, PVP 40, PVP K90, PVP 10), poly(maleic acid/methyl vinyl ether) (PMAMVE), (polyvinyl caprolactam-polyvinyl acetate-polyethylene glycol graft copolymer (e.g; Soluplus), polyoxyl 15 hydroxystearate (e.g; Solutol HS15), ethylene oxide/propylene oxide tetra functional block copolymer (e.g.; Tetronic 1107), and d-alpha tocopheryl polyethylene glycol 1000 succinate (TPGS); said complexes characterized in that they possess at least one of the following properties:
  a) are instantaneously redispersible in physiological relevant media
  b) are stable in solid form and in colloid solution and/or dispersion;
  c) have an apparent solubility in water of at least 1 mg/mL;
  d) have a PAMPA permeability of at least $0.5 \times 10^{-6}$ cm/s when dispersed in FaSSIF or FeSSIF biorelevant media, which does not decrease in time at least for 1 month; and
  e) have a PAMPA permeability of at least $0.4 \times 10^{-6}$ cm/s when dispersed in simulated saliva at pH=6.8.

In an embodiment, said complex formulations have instantaneous redispersibility, increased apparent solubility and permeability that provide faster onset of action for acute pain relief, eliminate the delay of peak plasma concentrations and lower GI related side effects compared to the currently available formulations.

In an embodiment, said complex formulations show X-ray amorphous character in the solid form.

It has been found that only the selected combinations of complexation agents and pharmaceutically acceptable excipients result in a stable complex formulae having improved physicochemical characteristics and enhanced biological performance.

The expression Celecoxib is generally used for Celecoxib, or its salts or its derivatives. In an embodiment, said complexation agent is chosen from polyethylene glycol glycerides composed of mono-, di- and triglycerides and mono- and diesters of polyethylene glycol (e.g.; Gelucire 44/14, Gelucire 50/13), hydroxypropylcellulose (e.g; Klucell EF, Klucell LF), poloxamers (copolymers of ethylene oxide and propylene oxide blocks) (e.g; Poloxamer 407, Poloxamer 335, Poloxamer 188, Poloxamer 338), vinylpyrrolidone/vinyl acetate copolymer (e.g.; Kollidon VA64), poly(2-ethyl-2-oxazoline) (e.g; PEOX50, PEOX500), polyvinylpyrrolidone (e.g; Plasdone K-12, PVP 40, PVP K90, PVP 10), poly(maleic acid/methyl vinyl ether) (PMAMVE), (polyvinyl caprolactam-polyvinyl acetate-polyethylene glycol graft copolymer (e.g; Soluplus), polyoxyl 15 hydroxystearate (e.g; Solutol HS15), ethylene oxide/propylene oxide tetra functional block copolymer (e.g.; Tetronic 1107), and d-alpha tocopheryl polyethylene glycol 1000 succinate (TPGS).

In an embodiment, said complexation agent is polyvinylpyrrolidone.

In an embodiment, said polyvinylpyrrolidone is PVP-40 (average mol wt=40.000).

In an embodiment, said complexation agent is a copolymer of vinylpyrrolidone and vinylacetate.

In an embodiment, said copolymer of vinylpyrrolidone (VP) and vinylacetate (VA) is Kollidon VA 64 (Composition is VP:VA=60:40)

In an embodiment, said complexation agent is a poloxamer.

In an embodiment, said poloxamer is poloxamer 407.

In an embodiment, said complex further comprises at least one pharmaceutically acceptable excipient selected from the group of sodium lauryl sulfate (SDS), dioctyl sodium sulfosuccinate (DSS), cetylpyridinium chloride (CPC), sodium acetate (NaOAC), sodium deoxycolate (SDC), meglumine, D-mannitol, and lactose.

In an embodiment, said pharmaceutically acceptable excipient is sodium lauryl sulfate.

In an embodiment, said pharmaceutically acceptable excipient is lactose.

In an embodiment, said complexes have controlled particle size in the range between 10 nm and 500 nm.

In an embodiment, said particle size is between 10 nm and 200 nm.

In an embodiment, said complexes have an apparent solubility in water of at least 1 mg/mL.

In an embodiment, said complexes further comprise one or more additional active agents.

In an embodiment, said additional active agent is chosen from agents useful for the treatment of any type of cancer.

In an embodiment, said complexes provide faster onset of action for acute pain relief and lower GI related side effects compared to the currently available formulations.

In an embodiment, said complexes possess at least two of the properties described in a)-e).

In an embodiment, said complexes possess at least three of the properties described in a)-e).

In an embodiment, said complexes have an increased dissolution rate compared to Celebrex®.

Further disclosed herein is a stable complex comprising an active compound selected from the group of Celecoxib, its salt, or derivatives thereof; at least one complexation agent chosen from polyvinylcaprolactam-polyvinyl acetate-polyethylene-glycol graft copolymers; poloxamers; polyvinylpyrrolidone; copolymers of vinylpyrrolidone and vinylacetate; and poly(maleic acid-co-methyl-vinyl-ether); and at least one pharmaceutically acceptable excipient chosen from sodium lauryl sulfate and lactose; wherein said complexes obtained via a mixing process.

In an embodiment, said complexation agent is polyvinylpyrrolidone.

In an embodiment, said polyvinylpyrrolidone is PVP-40 (average mol wt=40.000).

In an embodiment, said complexation agent is a copolymer of vinylpyrrolidone and vinyl acetate.

In an embodiment, said copolymer of vinylpyrrolidone and vinyl acetate is Kollidon VA 64 (Composition is VP:VA=60:40).

In an embodiment, said complexation agent is a poloxamer.

In an embodiment, said poloxamer is poloxamer 407.

In an embodiment, said complex further comprises at least one pharmaceutically acceptable excipient selected from the group consisting of sodium lauryl sulfate, dioctyl sodium sulfosuccinate, cetylpyridinium chloride, sodium acetate, sodium deoxycolate, meglumine, D-mannitol and lactose.

In an embodiment, said pharmaceutically acceptable excipient is sodium lauryl sulfate.

In an embodiment, said pharmaceutically acceptable excipient is lactose.

In an embodiment, said complexes are obtained via a continuous flow mixing process.

In an embodiment, a complex comprises a complexation agent chosen from a polyvinylpyrrolidone, a copolymer of vinylpyrrolidone and vinyl acetate, and a poloxamer; and a pharmaceutically acceptable excipient chosen from sodium lauryl sulfate or lactose, in a total amount ranging from about 1.0 weight % to about 95.0 weight % based on the total weight of the complex.

In an embodiment, a complex comprises a complexation agent chosen from a polyvinylpyrrolidone, a copolymer of vinylpyrrolidone and vinyl acetate, and a poloxamer; and pharmaceutically acceptable excipient chosen from sodium lauryl sulfate and lactose; wherein said complexation agent and pharmaceutically acceptable excipient together comprise 50.0 weight % to about 95.0 weight % of the total weight of the complex.

Further disclosed herein is a process for the preparation of the complex, comprising the steps of mixing a solution of Celecoxib, its salt, or derivatives thereof, and at least one complexation agent chosen from polyethylene glycol glycerides composed of mono-, di- and triglycerides and mono- and diesters of polyethylene glycol (e.g.; Gelucire 44/14, Gelucire 50/13), hydroxypropylcellulose (e.g; Klucell EF, Klucell LF), poloxamers (copolymers of ethylene oxide and propylene oxide blocks)(e.g; Poloxamer 407, Poloxamer 335, Poloxamer 188, Poloxamer 338), vinylpyrrolidone/vinyl acetate copolymer (e.g.; Kollidon VA64), poly(2-ethyl-2-oxazoline) (e.g; PEOX50, PEOX500), polyvinylpyrrolidone (e.g; Plasdone K-12, PVP 40, PVP K90, PVP 10), poly(maleic acid/methyl vinyl ether) (PMAMVE), (polyvinyl caprolactam-polyvinyl acetate-polyethylene glycol graft copolymer (e.g; Soluplus), polyoxyl 15 hydroxystearate (e.g; Solutol HS15), ethylene oxide/propylene oxide tetra functional block copolymer (e.g.; Tetronic 1107), and d-alpha tocopheryl polyethylene glycol 1000 succinate (TPGS) with an aqueous solution containing optionally least one pharmaceutically acceptable excipient chosen from sodium lauryl sulfate and lactose.

In an embodiment, said process is performed in a continuous flow instrument.

In an embodiment, said continuous flow instrument is a microfluidic flow instrument.

In an embodiment, said pharmaceutically acceptable solvent is chosen from methanol, ethanol, 1-propanol, 2-propanol, acetone, acetonitrile, dimethyl-sulfoxide, tetrahydrofuran, methyl-ethyl ketone or combinations thereof.

In an embodiment, said pharmaceutically acceptable solvent is methanol.

In an embodiment, said pharmaceutically acceptable solvent is 2-propanol.

In an embodiment, said pharmaceutically acceptable solvent is 1-propanol.

In an embodiment, said pharmaceutically acceptable solvent and said aqueous solution are miscible with each other.

In an embodiment, said aqueous solution comprises 0.1 to 99.9% weight of the final solution.

In an embodiment, said aqueous solution comprises 50 to 90% weight of the final solution.

In an embodiment, said aqueous solution comprises 50 to 80% weight of the final solution.

In an embodiment, said aqueous solution comprises 50 to 70% weight of the final solution.

In an embodiment, said aqueous solution comprises 50 to 60% weight of the final solution.

In an embodiment, said aqueous solution comprises 45 to 55% weight of the final solution.

In an embodiment, said aqueous solution comprises 50% weight of the final solution.

In an embodiment, said aqueous solution comprises 5 to 45% weight of the final solution.

In an embodiment, said aqueous solution comprises 5 to 35% weight of the final solution.

In an embodiment, said aqueous solution comprises 5 to 25% weight of the final solution.

Disclosed herein is a pharmaceutical composition comprising the complex together with a pharmaceutically acceptable carriers.

In an embodiment, said composition is suitable for oral, pulmonary, rectal, colonic, parenteral, intracisternal, intravaginal, intraperitoneal, ocular, otic, local, buccal, nasal, or topical administration.

In an embodiment, said compositions are suitable for buccal and oral administration.

In an embodiment, said complexes are for use in the manufacture of a medicament for the treatment of osteoarthritis, rheumatoid arthritis, juvenile rheumatoid arthritis, ankylosing spondylitis, acute pain especially in cancer related acute pain, primary dysmenorrhea.

In an embodiment, said complexes are used for the treatment of osteoarthritis, rheumatoid arthritis, juvenile rheumatoid arthritis, ankylosing spondylitis, acute pain especially in cancer related acute pain, primary dysmenorrhea.

Disclosed herein is a method of treatment of osteoarthritis, rheumatoid arthritis, juvenile rheumatoid arthritis, ankylosing spondylitis, acute pain especially in cancer related acute pain, primary dysmenorrhea comprising administration of a therapeutically effective amount of complexes or pharmaceutical compositions as described herein.

In an embodiment, a method for reducing the therapeutically effective dosage of Celecoxib compared to commercially available Celebrex comprises oral administration of a pharmaceutical composition as described herein.

Further disclosed herein is a stable complex comprising
a. 10-40% by weight of Celecoxib, its salt, or derivatives thereof;
b. 35-70% by weight of a polyvinylpyrrolidone; and
c. 5-50% by weight of sodium lauryl sulfate wherein said complex has a controlled particle size in the range between 10 nm and 500 nm; and
wherein said complex is not obtained via a milling process, high pressure homogenization process, encapsulation process and solid dispersion processes.

In an embodiment, said complex is characterized by a Raman spectrum having shifts at 563, 629, 645, 743, 760, 798, 850, 900, 934, 976, 1063, 1129, 1164, 1187, 1201, 1235, 1376, 1450, 1473, 1499, 1521, 1558, 1600, 1618, 1668, 2926, and 3076 cm$^{-1}$.

In an embodiment, said complex is characterized by an ATR spectrum having shifts at 542, 565, 610, 627, 742, 759, 806, 839, 923, 976, 1017, 1082, 1097, 1132, 1161, 1219, 1235, 1272, 1287, 1375, 1423, 1436, 1462, 1496, 1656, 2851, 2920, and 2956 cm$^{-1}$.

In an embodiment, said particle size is between 10 nm and 200 nm.

In an embodiment, said polyvinylpyrrolidone is PVP-40 (average mol wt=40.000).

Further disclosed herein is a stable complex comprising
a. 5-30% by weight of Celecoxib, its salt, or derivatives thereof;
b. 40-80% by weight of a copolymer of vinylpyrrolidone and vinyl acetate; and
c. 1-30% by weight of sodium lauryl sulfate
wherein said complex has a controlled particle size in the range between 10 nm and 500 nm; and
wherein said complex is not obtained via a milling process, high pressure homogenization process, encapsulation process and solid dispersion processes.

In an embodiment, said particle size is between 10 nm and 200 nm.

In an embodiment, said complex is characterized by a Raman spectrum having shifts at 628, 643, 741, 798, 896, 932, 977, 1062, 1084, 1128, 1164, 1202, 1233, 1297, 1375, 1450, 1497, 1521, 1555, 1600, 1612, 1676, 1736, 2937, and 3076 cm$^{-1}$.

In an embodiment, said copolymer of vinylpyrrolidone and vinyl acetate is Kollidon VA 64 (Composition is VP:VA=60:40).

Further disclosed herein is a stable complex comprising
a. 5-30% by weight of Celecoxib, its salt, or derivatives thereof;
b. 30-65% by weight of a poloxamer; and
c. 15-60% by weight of lactose
wherein said complex has a controlled particle size in the range between 10 nm and 500 nm; and
wherein said complex is not obtained via a milling process, high pressure homogenization process, encapsulation process and solid dispersion processes.

In an embodiment, said particle size is between 10 nm and 200 nm.

In an embodiment, said complex is characterized by a Raman spectrum having shifts at 629, 641, 741, 797, 846, 859, 975, 1062, 1164, 1236, 1279, 1376, 1449, 1472, 1521, 1556, 1599, 1612, 2882, and 2934 cm$^{-1}$.

In an embodiment, said poloxamer is poloxamer 407.

In an embodiment, said complexes show reduced fed/fasted effect based on in-vivo studies.

In an embodiment, said complex shows significantly improved exposure, earlier $t_{max}$, and higher $C_{max}$ which will allow the oral administration and reduction of the dose.

In an embodiment, said complexes have a faster onset of action compared to the existing formulations.

In an embodiment, said complexes are instantaneously redispersible in physiological relevant media.

In an embodiment, said complexes are stable in solid form and in colloid solution and/or dispersion.

In an embodiment, said complexes have apparent solubility in water of at least 1 mg/mL.

In an embodiment, said complexes show X-ray amorphous characters in the solid forms.

In an embodiment, said complex has a PAMPA permeability of at least $1.5 \times 10^{-6}$ cm/s when dispersed in FaSSIF or FeSSIF biorelevant media, which does not decrease in time at least for 1 month.

In an embodiment, said complex has a PAMPA permeability of at least $1.4 \times 10^{-6}$ cm/s when dispersed in simulated saliva at pH=6.8.

The complexation agents and pharmaceutically acceptable excipients of the Celecoxib complex formulations are selected from the group of pharmaceutically acceptable nonionic, anionic, cationic, ionic polymers, surfactants and other types of excipients. The complexation agents themselves or together with the pharmaceutically accepted excipients have the function to form a complex structure with an active pharmaceutical ingredient through non-covalent secondary interactions. The secondary interactions can form through electrostatic interactions such as ionic interactions, H-bonding, dipole-dipole interactions, dipole-induced dipole interactions, London dispersion forces, π-π interactions, and hydrophobic interactions. The complexation agents, pharmaceutically accepted excipients and active ingredients are selected from the group of complexation agents, pharmaceutically accepted excipients and active ingredients which are able to form such complex structures through non-covalent secondary interactions.

In some embodiments, the compositions may additionally include one or more pharmaceutically acceptable excipients, auxiliary materials, carriers, active agents or combinations thereof. In some embodiments, active agents may include agents useful for the treatment of any type of cancer.

Another embodiment is the complex formulae of the Celecoxib with complexation agents and pharmaceutically acceptable excipients in which the complexation agents and pharmaceutically acceptable excipients are associated or interacted with the Celecoxib, such as the results of a mixing process or a continuous flow mixing process. In an embodiment, the structure of the complex Celecoxib formulations is different from the core-shell type milled particle, precipitated encapsulated particles, micelles and solid dispersions.

The pharmaceutical composition can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

The compositions can be formulated by adding different types of pharmaceutically acceptable excipients for oral administration in solid, liquid, local (powders, ointments or drops), or topical administration, and the like.

In an embodiment, the dosage form is a solid dosage form, although any pharmaceutically acceptable dosage form can be utilized.

Solid dosage forms for oral administration include, but are not limited to, capsules, tablets, pills, powders (sachet), and granules. In such solid dosage forms, the complex formula of Celecoxib is admixed with at least one of the following: one or more inert excipients (or carriers): (a) fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide; (b) sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid; (c) binders, such as cellulose derivatives, acrylic acid derivatives, alginates, gelatin, polyvinylpyrrolidone, starch derivatives, dextrose, dextrates, dextrin, maltose, maltodextrin; (d) disintegrating agents, such as crospovidon, effervescent compositions, croscarmellose sodium and other cellulose derivatives, sodium starch glycolate and other starch derivatives, alginic acid, certain complex silicates and sodium carbonate; (e) solution retarders, such as acrylates, cellulose derivatives, paraffin; (f) absorption accelerators, such as quaternary ammonium compounds; (g) wetting agents, such as polysorbates, cetyl alcohol and glycerol monostearate; (h) lubricants such as talc, stearic acid and its derivatives, solid polyethylene glycols, sodium lauryl sulfate, glyceryl behenate, medium-chain triglycerides or mixtures thereof. For capsules, tablets, and pills, the dosage forms may also comprise buffering agents.

In an embodiment, the dosage form is chosen from a liquid dispersible granule, sachet, orodispersible tablet, orally dissolving tablet or chewing tablet.

In an embodiment, said liquid dispersible granules comprise the complex formulation of Celecoxib together with pharmaceutically acceptable excipients selected from the group consisting of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide.

In an embodiment, said liquid dispersible granules comprise the complex formulation of Celecoxib together with pharmaceutically acceptable excipients selected from the group consisting of sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein is a liquid dispersible granules comprising
 a. 25-95% stable complex formulation of Celecoxib;
 b. 5-75% fillers or extenders;
 c. 0.5-25% binders;
 d. 0.1-5% sweetening, flavoring, and perfuming agents;
wherein said liquid dispersible granules disperses within 10 min in liquid; and wherein said liquid dispersible granules are obtained by wet or dry processes.

In an embodiment, said dispersion time is between 0.1 min and 10 min.

In an embodiment, said dispersion time is between 0.1 min and 5 min.

In an embodiment, said dispersion time is between 0.1 min and 3 min.

In an embodiment, said dispersion time is between 0.1 min and 1 min.

In an embodiment, Hausner-ratio of the said liquid dispersible granules of complex celecoxib formulations is less than 1.25.

In an embodiment, Hausner-ratio of the said liquid dispersible granules of complex celecoxib formulations is between 1.00 and 1.11.

In an embodiment, the particle size (D(90)) of said solid aggregates of complex celecoxib formulations is less than 2000 micrometers.

In an embodiment, 60-80% of the said solid aggregates of complex celecoxib formulations are in the size range of 160-800 micrometers In an embodiment, said liquid is chosen from water, saliva, other physiologically or biologically acceptable fluid or liquid.

In an embodiment, the dosage form is chosen from a liquid dispersible granule, sachet, orodispersible tablet, orally dissolving tablet or chewing tablet.

In an embodiment, said liquid dispersible granules, sachet, orodispersible tablet, orally dissolving tablet or chewing tablet comprise the complex formulation of Celecoxib together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol.

In an embodiment, said liquid dispersible granules, sachet, orodispersible tablet, orally dissolving tablet or chewing tablet granules comprise the complex formulation of Celecoxib together with pharmaceutically acceptable excipients selected from the group of sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein is liquid dispersible granules, sachet, orodispersible tablet, orally dissolving tablet or chewing tablet comprising
 a. 25-95% stable complex formulation of Celecoxib;
 b. 0.5-75% fillers or extenders such as lactose, sucrose, glucose, mannitol, sorbitol, dextrose, dextrates, dextrin, erythritol, fructose, isomalt, lactitol, maltitol, maltose, maltodextrin, trehalose, xylitol;
 c. 0.1-5% sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid;
 d. 0.1-15% docusate sodium, sodium dodecyl sulfate, ammonium lauryl ether sulfate, benzalkonium chloride, benzethonium chloride, cetyl trimethylammonium bromide, polyoxyethelene alkylphenylethersm poloxamers, polyoxyethelene fatty acid glycerides, sorbitan esters;
wherein said liquid dispersible granules, sachet, orodispersible tablet, orally dissolving tablet or chewing tablet disperse within 10 min; and wherein said liquid dispersible granules obtained by wet or dry processes.

In an embodiment, said dispersion time is between 0.1 min and 3 min.

In an embodiment, said dispersion time is between 0.1 min and 1 min.

In an embodiment, the dosage form is chosen from a liquid dispersible granule, sachet, orodispersible tablet, orally dissolving tablet or chewing tablet.

The complex Celecoxib formulations disclosed herein show improvements including, but not limited to (1) physical and chemical stability, (2) instantaneous redispersibility, (3) stability in colloid solution or dispersion in the therapeutic time window, (4) increased apparent solubility and permeability compared to the conventional Celecoxib formulation, (5) decreased time to onset of action for acute pain, (6) oral bioavailability, (7) decreased fed/fasted effect especially with respect to $t_{max}$ and time to onset of action and (8) good processability.

The complex Celecoxib formulations disclosed herein display: the good/instantaneous redispersibility of solid complex formulations of Celecoxib in water, biologically relevant media, e.g.; physiological saline solution, pH=2.5 HCl solution, FessiF and FassiF media and gastro intestinal fluids and adequate stability in colloid solutions and/or dispersion in the therapeutic time window.

In an embodiment, the complex Celecoxib formulations have increased apparent solubility and PAMPA permeability. In some embodiments, the apparent solubility and permeability of the complex Celecoxib formulations is at least 1 mg/mL and $0.4 \times 10^{-6}$ cm/s, respectively.

In another embodiment, said complex Celecoxib formulations have an enhanced pharmacokinetic performance. The complex Celecoxib formulations show decreased $t_{max}$ and time to onset of action when compared to the current oral formulation.

BRIEF DESCRIPTION OF THE DRAWINGS

The accompanying figures, which are incorporated and form part of the specification, merely illustrate certain non-limiting embodiments. They are meant to serve to explain specific modes to those skilled in the art.

FIG. 1. shows the redispersibility of complex Celecoxib formulations in ultrapurified water.

FIG. 2. shows the redispersibility of complex Celecoxib formulations in simulated saliva.

FIG. 3. shows the PAMPA permeability of selected complex Celecoxib formulations.

FIG. 4. shows the composition optimization of complex Celecoxib formulation containing polyvinylpyrrolidone and sodium lauryl sulfate.

FIG. 5. shows the manufacturing process intensification and process parameter optimization.

FIG. 6. shows the optimization of the ratio of Solution 1 and Solution 2.

FIG. 7. shows the optimization of the production rate.

FIG. 8. shows the dissolution of Celecoxib from different solid forms.

FIG. 9. shows the PAMPA permeability of complex Celecoxib formulations in simulated saliva (pH=6.8).

FIG. 10. shows the PAMPA permeabilities of complex Celecoxib formulations containing polyvinylpyrrolidone and sodium lauryl sulfate.

FIG. 11. shows the PAMPA permeabilities of complex Celecoxib formulations containing copolymer of vinylpyrrolidone and vinyl acetate and sodium lauryl sulfate.

FIG. 12. shows the PAMPA permeabilities of complex Celecoxib formulations containing polyvinylpyrrolidone and sodium lauryl sulfate.

FIG. 13. shows the PAMPA permeabilities of complex Celecoxib formulations containing copolymer of vinylpyrrolidone and vinyl acetate and sodium lauryl sulfate.

FIG. 15A. shows the SEM images of Complex Celecoxib formulation containing polyvinylpyrrolidone and sodium lauryl sulfate.

FIG. 15B. shows the SEM images of Complex Celecoxib formulation containing copolymer of vinylpyrrolidone and vinyl acetate and sodium lauryl sulfate.

FIG. 15C. shows the SEM images of Complex Celecoxib formulation containing poloxamer and lactose.

FIG. 16A. shows the Raman spectra of unformulated crystalline Celecoxib.

FIG. 16B. shows the Raman spectra of Complex Celecoxib formulation containing polyvinylpyrrolidone and sodium lauryl sulfate.

FIG. 16C. shows the Raman spectra of Placebo sample containing polyvinylpyrrolidone and sodium lauryl sulfate.

FIG. 16D. shows the Raman spectra of Polyvinylpyrrolidone.

FIG. 16E. shows the Raman spectra of Sodium lauryl sulfate.

FIG. 17A. shows the Raman spectra of unformulated crystalline Celecoxib.

FIG. 17B. shows the Raman spectra of Complex Celecoxib formulation containing polyvinylpyrrolidone and sodium lauryl sulfate.

FIG. 17C. shows the Raman spectra of Complex Celecoxib formulation containing copolymer of vinylpyrrolidone and vinyl acetate and sodium-lauryl-sulfate.

FIG. 17D. shows the Raman spectra of Complex Celecoxib formulation containing poloxamer and lactose.

FIG. 18A. shows the ATR spectra of unformulated crystalline Celecoxib.

FIG. 18B. shows the ATR spectra of Complex Celecoxib formulation containing polyvinylpyrrolidone and sodium lauryl sulfate.

FIG. 18C. shows the ATR spectra of Placebo sample containing polyvinylpyrrolidone and sodium lauryl sulfate.

FIG. 18D. shows the ATR spectra of Polyvinylpyrrolidone.

FIG. 18E. shows the ATR spectra of Sodium-lauryl-sulfate.

FIG. 19A. shows the Powder XRD diffractograms of Complex Celecoxib formulation containing polyvinylpyrrolidone and sodium lauryl sulfate.

FIG. 19B. shows the Powder XRD diffractograms of Complex Celecoxib formulation containing copolymer of vinylpyrrolidone and vinyl acetate and sodium lauryl sulfate.

FIG. 19C. shows the Powder XRD diffractograms of Complex Celecoxib formulation containing poloxamer and lactose.

FIG. 20. shows the PK parameters of complex Celecoxib formulations in Beagle dogs.

FIG. 21. shows the PK parameters of complex Celecoxib formulations in Beagle dogs in fasted and fed condition.

FIG. 22. shows the PK parameters of complex Celecoxib formulations in healthy volunteers in fasted and fed condition.

EXAMPLES

Figure 14:
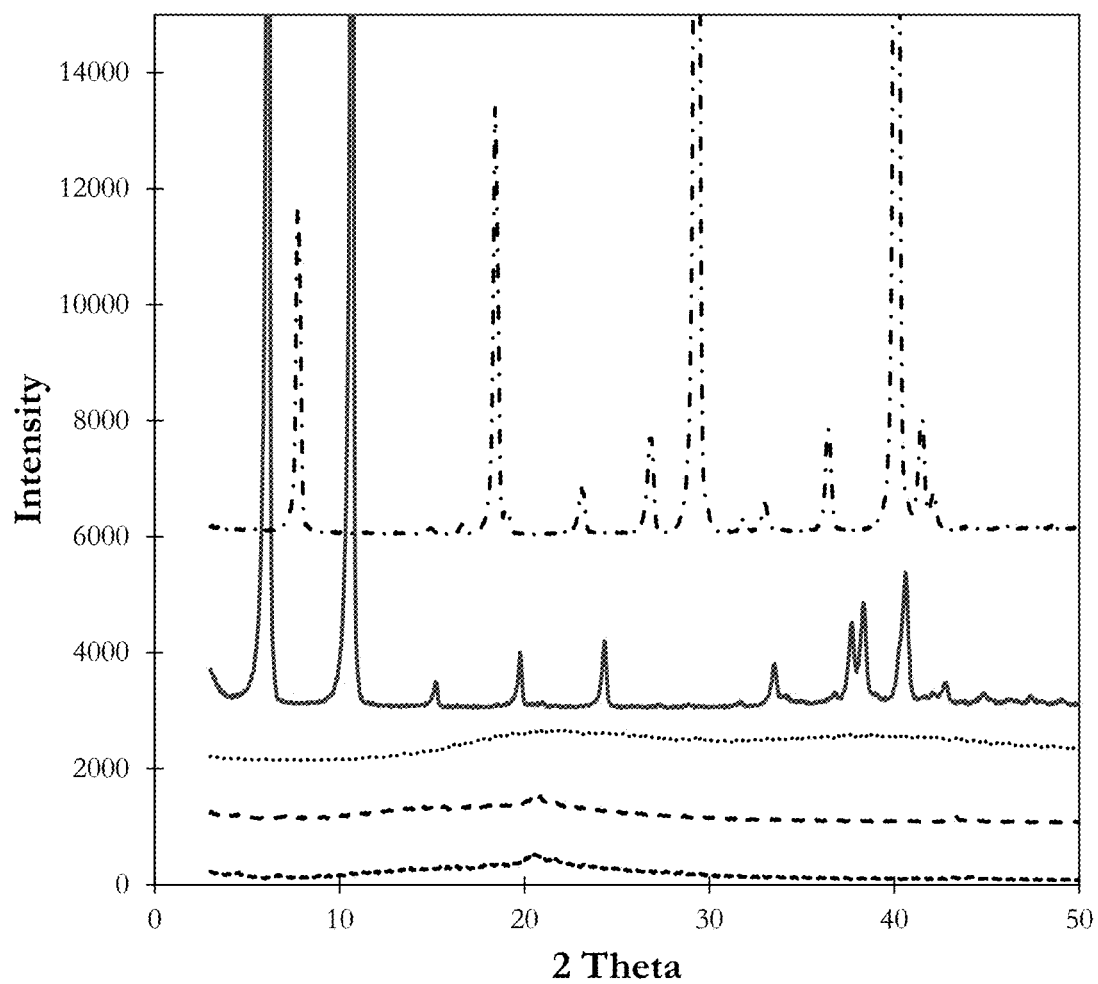
FIG. 14. shows the PXRD diffractograms of complex Celecoxib formulations containing copolymer of vinylpyrrolidone and vinyl acetate and sodium lauryl sulfate at different time points.

Specific non-limiting embodiments will further be demonstrated by the following examples.

Selection of Complex Celecoxib Formulations with Improved Material Properties

Several complexation agents and pharmaceutically acceptable excipients and their combinations were tested in order to select the formulae having instantaneous redispersibility as shown in FIG. 1 and FIG. 2.

Examples that displayed an acceptable level of redispersibility was selected for further analysis.

PAMPA permeability of the selected formulations was measured in order to select the complex Celecoxib formulation having the best in-vitro performance (FIG. 3). PAMPA permeability measurements were performed as described by M. Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 4 hours in ultrapurified water or 10-20 and 30 minutes in simulates saliva, respectively. The concentration in the receiver compartment was determined by UV-VIS spectrophotometry (Thermo Scientific Genesys S10).

Polyvinylpyrrolidone and sodium lauryl sulfate were selected as the complexation agent and pharmaceutically acceptable excipient, respectively, to form complex Celecoxib formulation having improved material characteristics.

Copolymer of vinylpyrrolidone and vinyl acetate and sodium lauryl sulfate were selected as the complexation agent and pharmaceutically acceptable excipient, respectively, to form complex Celecoxib formulation having improved material characteristics.

Poloxamer F127 and lactose were selected as the complexation agent and pharmaceutically acceptable excipient, respectively, to form complex Celecoxib formulation having improved material characteristics.

Composition Optimization and Manufacturing of Complex Celecoxib Formulations

The ratio of the selected complexation agents and pharmaceutically acceptable excipients was optimized. Solid complexes of Celecoxib were prepared by using different ratios of complexation agents and pharmaceutically acceptable excipients.

A solution mixture of Celecoxib complex formulation was prepared by continuous flow mixing in a flow instrument. 100 mL Solution 1 was prepared by dissolving 200 mg Celecoxib and 400 mg polyvinylpyrrolidone (PVP 40) in 100 mL methanol. The prepared Solution 1 was passed into the instrument with 1.25-2 mL/min flow rate. Meanwhile, Solution 2 containing 30-50 mg sodium lauryl sulfate in 100 mL water was passed into the instrument with 5-10 mL/min flow rate, where Celecoxib formed complex Celecoxib formulation. The solution mixture of the complex Celecoxib formulation is continuously produced at atmospheric pressure and ambient temperature. The produced solution mixture was frozen on dry-ice and then it was lyophilized using a freeze drier equipped with −110° C. ice condenser, with a vacuum pump.

The appearance of produced solution mixture and stability of the redispersed complex Celecoxib formulation were monitored. Based on the physical appearance and stability of the reconstituted solid complex Celecoxib formulation, the best composition was selected for analytical investigations (FIG. 4).

In order to make the production process industrially feasible, process intensification was performed by increasing the concentrations of the starting solutions. A solution mixture of complex Celecoxib formulation was prepared by mixing process. Methanolic Solution 1 containing 1.25-10 mg/mL Celecoxib and 2.5-20 mg/mL polyvinylpyrrolidone (PVP 40) was mixed with aqueous Solution 2 containing 0.2812-18 mg/mL sodium lauryl sulfate in different ratios in order to optimize the production condition. The solution mixture of the complex Celecoxib was produced at atmospheric pressure and ambient temperature. The produced solution mixture was frozen on dry-ice and then it was lyophilized using a freeze drier equipped with −110° C. ice condenser, with a vacuum pump.

Different concentrations and solvent ratios were tested to determine the optimal manufacturing condition. The stability of the produced solvent mixture was used to determine the optimal parameter of the production. FIG. 5 summarizes the results.

Based on the results, 10 mg/mL Celecoxib, 20 mg/mL polyvinylpyrrolidone and 18 mg/mL sodium lauryl sulfate were chosen for starting concentrations. The ratio of the solutions was found to be optimal at 2:1 ratio.

Solution mixture of complex Celecoxib formulation comprising polyvinylpyrrolidone and sodium lauryl sulfate and prepared by optimal parameter sets was spray-dried (Yamato DL-410/GAS410) in order to obtain solid powder. The spray-drying process was optimized. The optimal production parameters were found to be $T_{inlet}$=95° C., Drying airflow=0.8 m³/min, Solution feed rate=18 mL/min, atomization pressure=1 bar, $T_{out}$=63-64° C. The spray-dried formulation was granulated and used for iv-vivo dog PK studies. A solution mixture of complex Celecoxib formulation was prepared by mixing process. 2-propanolic Solution 1 containing 5 mg/mL Celecoxib and 20 mg/mL copolymer of vinylpyrrolidone and vinyl acetate (Kollidon VA64) was mixed with aqueous Solution 2 containing 1.25 mg/mL sodium lauryl sulfate. The solution mixture of the complex Celecoxib was produced at atmospheric pressure and ambient temperature. The ratio of the solutions was 1:4 (2-Propanol:Water). The produced solution mixture was frozen on dry-ice and then it was lyophilized using a freeze drier equipped with −110° C. ice condenser, with a vacuum pump.

Different flow rates and concentrations were tested in order to determine the optimal manufacturing condition. The appearance and stability of the produced solvent mixture was used to determine the optimal parameter of the production. FIG. 6 and FIG. 7 summarizes the results.

Based on the results, 10 mg/mL Celecoxib, 40 mg/mL copolymer of vinylpyrrolidone and vinyl acetate and 20 mg/mL sodium lauryl sulfate were chosen as starting concentration. The ratio of Solution 1 and Solution 2 was found to be optimal at 2:1 ratio at 40 mL/min and 20 mL/min flow rate ratio.

The solution mixture of complex Celecoxib formulation prepared by the optimal parameter sets was spray-dried (Yamato DL-410/GAS410). The spray-drying process was optimized. Optimal production parameters were found to be $T_{inlet}$=95° C., Drying airflow=0.8 m³/min, Solution feed rate=18 mL/min, atomization pressure=1 bar, $T_{out}$=63-64° C. The spray-dried formulation was granulated and used for iv-vivo dog PK studies.

The solution mixture of complex Celecoxib formulation comprising copolymer of vinylpyrrolidone and vinyl acetate and sodium lauryl sulfate prepared by optimal parameter sets was spray-dried (Procept 4M-8Trix) in order to obtain solid powder. Production process was performed under cGMP condition to support the Phase I human clinical study. Optimal production parameters were found to be $T_{inlet}$=135° C., drying airflow=0.3 m³/min, solution feed rate=3-4 g/min, atomization pressure=1-3 bar, atomization flow=19 L/min $T_{out}$=70-72° C. and the diameter of the nozzle was 0.8 mm. The spray-dried formulation was granulated and used for Phase 1 human clinical study. A solution mixture of complex Celecoxib formulation was prepared by mixing process. 1-propanolic Solution 1 containing 2 mg/mL Celecoxib and 6 mg/mL Poloxamer 407 (Lutrol F127) was mixed with aqueous Solution 2 containing 1 mg/mL lactose. The solution mixture of the complex Celecoxib was produced at atmospheric pressure and ambient temperature. The ratio of the solutions was 1:4 (1-Propanol:Water). The produced solution mixture was frozen on dry-ice and then it was lyophilized using a freeze drier equipped with −110° C. ice condenser, with a vacuum pump.

Pharmaceutical Development

Liquid dispersible granules comprising said complex Celecoxib formulations may be obtained by wet or dry processes.

Liquid dispersible granules comprising said complex Celecoxib formulations were obtained by dry process. Compacts with uniform dimensions and mass were prepared of the solid complex Celecoxib formulations. The compacts were broken up by physical impact in order to form granulates within appropriate mesh size. After that granulates were mixed with pharmaceutically acceptable excipients.

Liquid dispersible granules comprising said complex Celecoxib formulations were obtained by dry process. The solid Celecoxib formulations were mixed with pharmaceutically acceptable excipients. After that compacts with uniform dimensions and mass were prepared of the powder mixtures comprising said complex formulations of Celecoxib. The compacts were broken up by physical impact in order to form granulates within appropriate mesh size.

Liquid dispersible granules for buccal and oral administrations were prepared by compacting 40 mg solid complex Celecoxib formulation comprising polyvinylpyrrolidone and sodium lauryl sulfate using 0.5 ton load. The height of the compact was found to be optimal between 0.8-1.0 mm. The compacts were broken up by physical impact to form granulates. The particle size of the granulates was controlled by sieving with appropriate mesh size to achieve 160-800 micrometers particle size.

Liquid dispersible granules for oral administration were prepared by compacting 500 mg solid complex Celecoxib formulation comprising copolymer of vinylpyrrolidone and vinyl acetate and sodium lauryl sulfate using 3 ton load. The height of the compact was found to be optimal between 4-6 mm. The compacts were broken up by physical impact to form granulates. The particle size of the granulates was controlled by sieving with appropriate mesh size to achieve 160-800 micrometers particle size.

Liquid dispersible granules for oral administration were prepared from the spry-dried powder by compacting 1900 mg solid complex Celecoxib formulation comprising copolymer of vinylpyrrolidone and vinyl acetate and sodium lauryl sulfate using a flat faced tooling with 22 mm diameter and pressed with 3 ton load. The height of the compact was found to be optimal between 4.5-5.5 mm. The compacts were broken up by physical impact to form granulates. The particle size of the granulates was controlled by sieving with appropriate mesh size to achieve 150-850 micrometers particle size.

Liquid dispersible granules comprising said complex Celecoxib formulations were obtained by wet process. The pharmaceutically acceptable excipients were moisturized by water or aqueous binder solution. The solid complex Celecoxib formulations were mixed with the preliminary moisturized excipients to form granulates. After the drying step the particle size of the granulates was controlled by physical impact.

Liquid dispersible granules comprising said complex Celecoxib formulations were obtained by wet process. The pharmaceutically acceptable excipients were moisturized by the solvents mixtures comprising the complex Celecoxib formulations to form granulates. After the drying step the particle size of the granulates was controlled by physical impact.

Improved Apparent Solubility of Complex Celecoxib Formulation

The apparent solubility of said complex Celecoxib formulations were measured by UV-VIS spectroscopy at room temperature. The solid complex Celecoxib formulations were dispersed in ultrapurified in 1-50 mg/mL Celecoxib equivalent concentration range. The resulting solutions were filtered by 100 nm disposable syringe filter. The Celecoxib content in the filtrate was measured by UV-Vis spectrophotometry and the apparent solubility was calculated. The filtrate may contain Celecoxib complex particles which could not be filtrated out using 100 nm pore size filter.

The apparent solubility of said complex Celecoxib formulation comprising polyvinylpyrrolidone and sodium lauryl sulfate was 1.009; 10.334; 25.148 and 40.362 mg/mL, when 1; 10; 25 and 50 mg/mL Celecoxib equivalent formulations were dispersed in ultrapurified water, respectively.

The apparent solubility of said complex Celecoxib formulation comprising copolymer of vinylpyrrolidone and vinylacetate and sodium lauryl sulfate formulation was 1.015; 9.605; 22.358 and 34.142 mg/mL, when 1; 10; 25 and 50 mg/mL Celecoxib equivalent formulations were dispersed in ultrapurified water, respectively.

Solubility of complex Celecoxib formulae was 1 mg/mL.

Improved Dissolution Profile of Complex Celecoxib Formulation

Comparative dissolution tests were performed by dispersing the complex Celecoxib formulations, the physical mixtures of Celecoxib, complexation agents and excipients, unformulated crystalline Celecoxib and Celebrex (commercial formulation) in purified water at 1 mg/mL concentrations. The dissolved amount was measured with UV-VIS spectrophotometry after filtration with 0.1 μm pore size filter at different time points. Dissolution of Celecoxib from the complex formulation was instantaneous, within 10 min more than 90% of the Celecoxib dissolved from the complex Celecoxib formulations. The dissolution of Celecoxib from the physical mixture and Celebrex® was incomplete and slow.

Comparative In-Vitro PAMPA Assays

PAMPA permeabilities of complex Celecoxib formulations were above $0.5 \times 10^{-6}$ cm/s in simulated saliva condition, while it was $0.3 \times 10{-6}$ cm/s for the unformulated compound, see FIG. 9.

PAMPA permeabilities of complex Celecoxib formulations containing polyvinylpyrrolidone and sodium lauryl sulfate in water, FaSSIF and FeSSIF media were above $2.3 \times 10^{-6}$ cm/s, $1.9 \times 10^{-1}$ cm/s and $1.7 \times 10$ cm/s, respectively (FIG. 10). PAMPA permeabilities of complex Celecoxib formulations containing copolymer of vinylpyrrolidone and vinyl acetate and sodium lauryl sulfate in water, FaSSIF and FeSSIF media were above $2.1 \times 10^{-6}$ cm/s, $1.5 \times 10^{-6}$ cm/s and $2.6 \times 10^{-6}$ cm/s, respectively (FIG. 11).

Stability of the Solid Form

PAMPA permeabilities of the solid complex Celecoxib formulations containing polyvinylpyrrolidone and sodium lauryl sulfate were used to monitor the physical stability of the formulation. PAMPA permeability was measured after storage at different conditions. 1 month storage at RT or 40° C. and 75% relative humidity showed no significant decrease in the measured PAMPA permeability under any of the conditions tested (FIG. 12).

PAMPA permeabilities of the solid complex Celecoxib formulations containing copolymer of vinylpyrrolidone and vinylacetate and sodium lauryl sulfate were used to monitor the stability of the formulation. PAMPA permeability was measured after storage at different conditions. 6-month storage at RT or 40° C. and 75% relative humidity showed no significant decrease in the measured PAMPA permeability under any of the conditions tested (FIG. 13).

XRD diffractograms of the solid complex Celecoxib formulations containing copolymer of vinylpyrrolidone and vinylacetate and sodium lauryl sulfate were used to monitor the stability of the formulation. pXRD was measured after storage at different conditions. 6-month storage at RT or 40° C. and 75% relative humidity showed no crystallization under any of the conditions tested (FIG. 14).

Structural Analysis

Morphology of complex Celecoxib was investigated using FEI Quanta 3D scanning electron microscope. Complex Celecoxib formulations comprise spherical particles in the size range of less than 200 nm (FIG. 15).

Structural analysis was performed by using Bruker Vertex 70 FT-IR spectrometer with Bruker Platinum diamond ATR unit. Continuous flow mixing of Celecoxib in the presence of selected complexation agents and pharmaceutically acceptable excipients, resulted in a stable complex of Celecoxib.

In an embodiment said complex containing polyvinylpyrrolidone and sodium lauryl sulfate or its pharmaceutical compositions characterized by the Raman spectrum shown in FIG. 16 and ATR spectrum shown in FIG. 18.

In an embodiment said complex containing copolymer of vinylpyrrolidone and vinyl acetate and sodium lauryl sulfate or its pharmaceutical composition is characterized by the Raman spectrum shown in FIG. 17 and ATR spectrum shown in FIG. 18.

In an embodiment said complex containing poloxamer and lactose or its pharmaceutical composition is characterized by the Raman spectrum shown in FIG. 17 and ATR spectrum shown I in FIG. 18.

The structures of the complex Celecoxib formulations were investigated by powder X-ray diffraction (XRD) analysis (Philips PW1050/1870 RTG powder-diffractometer). The measurements showed that the Celecoxib in the complex formulations was XRD amorphous (See FIG. 19). Characteristic reflections on the diffractograms of complex Celecoxib formulation at 43 and 44 2Theta could be attributed to sample holder.

In-Vivo Pharmacokinetics

In-Vivo PK Test in Large Animals

A beagle dog study using the granulated complex formulation containing polyvinylpyrrolidone and sodium lauryl sulfate at a dose of 5 mg/kg was performed in the fasted and in the fed state following a high fat meal. The granulated complex formulation containing polyvinylpyrrolidone and sodium lauryl sulfate was administered under the tongue of the animals as the granule or orally as reconstituted dispersion, respectively. The absorption of the Celecoxib was fast with $t_{max}$ values at 1-2 hours with 65% of $C_{max}$ reached within 0.5 hours, when the granulated complex formulation containing polyvinylpyrrolidone and sodium lauryl sulfate formulation was administered under the tongue of the animals (FIG. 20). The absorption of the Celecoxib was fast with $t_{max}$ value at 0.5 hours with 70% of $C_{max}$ reached within 0.25 hours when the granulated complex formulation containing polyvinylpyrrolidone and sodium-lauryl-sulfate formulation was administered orally (FIG. 20).

A beagle dog study using the granulated complex formulation containing copolymer of vinylpyrrolidone and vinyl acetate and sodium lauryl sulfate at a dose of 5 mg/kg was performed in fasted and the fed state following a high fat meal. The granulated complex formulation containing copolymer of vinylpyrrolidone and vinyl acetate and sodium lauryl sulfate was administered orally as reconstituted dispersion. The absorption of Celecoxib was fast with $t_{max}$ values at 0.75-1 hours with 90% of $C_{max}$ reached within 0.5 hours, when the granulated complex formulation containing copolymer of vinylpyrrolidone and vinyl acetate and sodium lauryl sulfate formulation was administered orally both in the fasted state of following a high-fat meal (FIG. 21).

Phase I Clinical Trial

A Human phase I clinical study was performed using the copolymer of vinylpyrrolidone and vinylacetate and sodium lauryl sulfate. The granulated complex formulation containing copolymer of vinylpyrrolidone and vinylacetate and sodium lauryl sulfate was administered orally as reconstituted dispersion. The clinical methodology was a single center, open-label, non-randomized, single dose, fixed sequence crossover study in 12 healthy male subjects. Each subject received 200 mg Celecoxib formulation in the fasted state or following a high-fat meal breakfast. The absorption of the Celecoxib was fast with $t_{max}$ values at 0.75 and 2 hours in the fasted state and following a high-fat breakfast, respectively. Regardless of feeding conditions the effective plasma concentration (250 ng/ml) was achieved within 12 minutes following administration when the granulated complex formulation containing copolymer of vinylpyrrolidone and vinyl acetate and sodium lauryl sulfate formulation was administered orally (FIG. 22).

From the foregoing description, one skilled in the art can easily ascertain the essential characteristics of this invention, and without departing from the spirit and scope thereof, can make various changes and modifications to adapt it to various usages and conditions.

What is claimed is:

1. A pharmaceutical composition in the form of liquid dispersible granules comprising:
   amorphous celecoxib;
   at least one complexation agent that is a copolymer of vinylpyrrolidone and vinyl acetate;
   at least one pharmaceutically acceptable excipient that is sodium lauryl sulfate; and
   at least one sweetener chosen from aspartame, neotame, sucralose, acesulfame potassium, saccharin, and saccharin sodium,
   said complex characterized in that it has a PAMPA permeability of at least $0.5 \times 10^{-6}$ cm/s when dispersed in FaSSIF or FeSSIF biorelevant media, which does not decrease in time at least for 1 month.

2. The pharmaceutical composition of claim 1, wherein the amorphous celecoxib is present in an amount of between 5 and 30% by weight.

3. The pharmaceutical composition of claim 1, wherein the at least one complexation agent is present in an amount of between 40 and 80% by weight.

4. The pharmaceutical composition of claim 1, wherein the at least one pharmaceutically acceptable excipient is present in an amount of between 1 and 30% by weight.

5. The pharmaceutical composition of claim 3, wherein said at least one complexation agent and said at least one pharmaceutically acceptable excipient are present in an amount of between 50 and 95 weight %.

6. The pharmaceutical composition of claim 1, wherein the at least one sweetener is saccharin sodium.

7. A reconstituted dispersion comprising the liquid dispersible granules of claim 1 dispersed in a liquid.

8. A method of treatment of osteoarthritis, rheumatoid arthritis, juvenile rheumatoid arthritis, ankylosing spondylitis, acute pain, or primary dysmenorrhea comprising administration of a therapeutically effective amount of the pharmaceutical composition of claim 1 to a subject in need thereof.

9. A method of treatment of osteoarthritis, rheumatoid arthritis, juvenile rheumatoid arthritis, ankylosing spondylitis, acute pain, or primary dysmenorrhea comprising administration of a therapeutically effective amount of the reconstituted dispersion of claim 7 to a patient in subject thereof.

\* \* \* \* \*